United States Patent [19]

Jost

[11] Patent Number: 4,649,075
[45] Date of Patent: Mar. 10, 1987

[54] TRANSDERMAL AND TRANSMUCOSAL VORTEXED FOAM DEVICES AND THE METHOD OF MAKING

[76] Inventor: Leonora Jost, R.R. 1, Box 130, Oxford, Me. 04270

[21] Appl. No.: 639,097

[22] Filed: Aug. 9, 1984

[51] Int. Cl.⁴ .................. A61M 31/00; A61F 13/20; A61L 15/00
[52] U.S. Cl. .................. 428/305.5; 428/316.6; 428/905; 424/449
[58] Field of Search .............. 424/15, 22; 604/892; 428/905, 305.5, 316.6

[56] References Cited

U.S. PATENT DOCUMENTS

| | | | |
|---|---|---|---|
| 2,561,071 | 7/1951 | Prisk | 604/896 |
| 3,598,122 | 8/1971 | Zaffaroni | 604/897 |
| 3,636,922 | 1/1972 | Ketner | 514/947 |
| 3,948,254 | 4/1976 | Zaffaroni | 604/892 |
| 3,993,072 | 11/1976 | Zaffaroni | 604/892 |
| 4,008,719 | 2/1977 | Theeuwes et al. | 604/895 |
| 4,014,334 | 3/1977 | Theeuwes et al. | 604/896 |
| 4,058,122 | 11/1977 | Theeuwes et al. | 424/19 |
| 4,077,407 | 3/1978 | Theeuwes et al. | 424/20 |
| 4,116,241 | 9/1978 | Theeuwes et al. | 424/21 |
| 4,220,152 | 9/1980 | Dresback | 604/892 |
| 4,220,153 | 9/1980 | Dresback | 604/892 |
| 4,223,061 | 9/1980 | Michaels | 604/892 |
| 4,235,236 | 11/1980 | Theeuwes et al. | 604/892 |
| 4,235,988 | 11/1980 | Fildes et al. | 604/892 |
| 4,237,888 | 12/1980 | Roseman et al. | 604/892 |
| 4,278,087 | 7/1981 | Theeuwes et al. | 604/892 |
| 4,289,749 | 9/1981 | Keith et al. | 424/28 |
| 4,290,426 | 9/1981 | Luschen et al. | 604/892 |
| 4,291,015 | 9/1981 | Keith et al. | 424/28 |
| 4,298,003 | 11/1981 | Theeuwes et al. | 604/892 |
| 4,300,558 | 11/1981 | Eckenhoff et al. | 604/892 |
| 4,304,232 | 12/1981 | Michaels | 604/892 |
| 4,308,867 | 1/1982 | Roseman et al. | 604/892 |
| 4,309,996 | 1/1982 | Theeuwes | 604/892 |
| 4,314,557 | 2/1982 | Chandrasekaran | 604/892 |
| 4,320,759 | 3/1982 | Theeuwes | 604/892 |
| 4,326,525 | 4/1982 | Swanson et al. | 604/892 |
| 4,350,271 | 9/1982 | Eckenhoff | 604/892 |
| 4,367,741 | 1/1983 | Michaels | 222/95 |
| 4,379,454 | 4/1983 | Campbell et al. | 604/897 |
| 4,409,206 | 10/1983 | Stricker | 424/81 |
| 4,435,180 | 3/1984 | Leeper | 604/896 |
| 4,449,983 | 5/1984 | Cortese et al. | 604/892 |
| 4,450,844 | 5/1984 | Quisno | 128/743 |
| 4,460,368 | 7/1984 | Allison et al. | 604/896 |
| 4,460,369 | 7/1984 | Seymour | 604/897 |
| 4,460,372 | 7/1984 | Campbell et al. | 604/897 |
| 4,538,603 | 9/1985 | Pawelchak et al. | 604/897 |

Primary Examiner—Ronald W. Griffin
Attorney, Agent, or Firm—Memel, Jacobs & Ellsworth

[57] ABSTRACT

A device for delivery of medicaments to epidermal and mucosal surfaces, comprising a microporous outer portion made from polymeric foam, and a macroporous inner portion made from polymeric foam disposed within the outer portion and in substantial communication with the outer portion which is adapted for incorporating a medicament therein, wherein the macroporous inner portion has at least one free surface not in communication with the microporous outer portion, and the pore size ratio of the macroporous inner portion to the microporous outer portion is between about 2 to 1 and 1.67 to 1.

23 Claims, 1 Drawing Figure

TRANSDERMAL AND TRANSMUCOSAL VORTEXED FOAM DEVICES AND THE METHOD OF MAKING

FIELD OF INVENTION

The present invention relates to therapeutic delivery systems, and more particularly to transdermal and transmucosal systems that administer a drug, medicament or other substance at a controlled and predefined rate, for a prolonged and determined period of time, to a defined body region for either local or systemic action. Also encompassed by the present invention are delivery systems with the above-mentioned features but for local delivery within the lumen of a body cavity.

BACKGROUND OF THE INVENTION

Various therapeutic delivery devices and systems which reportedly provide some or all of the above-mentioned advantageous features are known in the art. Such delivery devices and systems may be classified according to their delivery means, such as, e.g., diffusional, osmotic, elastomeric, or mechanically facilitated devices, and erodible or nonerodible systems. The novel devices of the present invention are nonerodible diffusion systems which take advantage of Bernoulli effects to perform their function.

A major benefit of the transdermal systems such as those within the scope of the present invention is the elimination of the characteristic swings in medicament concentration within the body of the patient that are common when parenteral administration of medicaments is employed. It is common to overmedicate so that the body will receive enough medication to allow long term effectiveness. Unfortunately, high initial doses or widely fluctuating dose levels, may cause adverse side effects within the body of the patient. Transdermal methods of applying medicament provide a relatively long term and continuous supply of the medicament and thus eliminate the need for the over medication peak necessary with intravenous administration. Transdermal devices such as those embodied by the present invention have the further advantage over intravenous methods in that no trauma results from use of these devices.

Problems associated with oral methods of supplying medicaments in mammalian systems are also overcome by transdermal and transmucosal devices. Lesions of the tongue, esophagus and stomach have been shown to often accompany constant use of such oral medicaments as aspirin and in some cases this use has been shown to cause in situ tumors. Transdermal devices avoid this potential problem by fixing the site of medicament transfer on the skin or a mucous membrane and by supplying the medicament in lower and constant concentrations. These devices provide the additional benefit of localized treatment, i.e., the device may be affixed directly to the afflicted region to provide specific treatment of regional disorders such as tumors.

In order to ameliorate the above mentioned problems, various under the skin implants, pumps and strips of medicated materials have been heretofore proposed. Although these devices are represented to release medicament at a constant concentration level for a predetermined period of time, they are costly, require careful monitoring by a physician and they often pose an added danger of serving as a focus for bacterial infection.

There are also other systems for transferring medicament across dermal or mucosal surfaces that are more nearly related to the present invention, because they rely on diffusion for the subcutaneous transfer of active agent to the circulating system at the interface between the applicator and the patient's skin, although each employs different driving forces to supply the chemical energy necessary for effective transdermal transfer from the Bernoulli effects on which the present invention depends. In this invention, Bernoulli effects are availed of to apply concentrated solutions of the active agent to the skin at a rate and pressure sufficient for optimal absorption. No previously disclosed transdermal delivery device operates in this manner.

Many patented devices rely exclusively on diffusion for transporting active agents. Such devices do not provide the efficient directed flow of the agent against the skin that can be provided by the present use of the Bernoulli effect. Often such devices are designed to release agents into a liquid containing environment within the body, such as the gastrointestinal tract, or if used for transdermal applications, these devices must include some type of cover to prevent the agent from being released to the surrounding environment, whether by evaporation or other means. The present invention is instead designed for unidirection transfer of medicament against the skin or mucous membrane to which it is attached. Typical diffusion-type devices are described in the following paragraphs.

U.S. Pat. No. 4,291,015 describes a polymeric diffusion matrix containing a vasodilator comprising a polar plasticizer, such as glycerol, a polymeric matrix, and a water soluble polymer along with the vasodilator. The transdermal transfer of the active ingredient is effected by use of a diffusion concentration gradient normal to the surface of the patient's skin and the diffusion matrix. An inert backing material is affixed to the side of the device not in contact with the patient's skin.

U.S. Pat. No. 4,220,153 discloses a delivery device comprising a porous fabric impregnated with a hydrogel surrounding a chemical containing reservoir, which may include a drug and a water soluble liquid incipient. This device is designed to be used primarily in an aqueous liquid containing environment within the body since the diffusional mechanism requires bidirectional mass transfer.

U.S. Pat. No. 4,308,867 describes a diffusion device which is comprised of an inner support, a polymeric layer containing an active agent, and an outer polymeric membrane. The two polymeric layers are chosen based on their relative diffusion coefficients and solubilities so that the rate of release of the active agent into the external environment can be controlled. Here again the mechanism of release is only diffusion.

Many patented devices rely on osmotic pumping to supply the pressure necessary for the system to operate. For example, U.S. Pat. No. 4,008,719 discloses such a device wherein the active agent is contained in an internal compartment which is surrounded by plural semipermeable laminae. The laminae allow unhindered passage of the driving fluid but prevent passage of the active agent, thus setting up a net transfer of material into the inner compartment and supplying osmotic pressure. Such devices suffer from the disadvantage of relative structural complexity and are expensive to make because they require sophisticated manufacturing techniques; this in turn makes them expensive to use.

Another means for supplying the force necessary to cause the active agent to be released from transdermal applicators is through mechanical pressure. Several patented devices rely upon swellable polymers which when contacted with fluid expand causing a decrease in the volume available for the active agent. The resulting pressure increase drives the agent from the system into the desired environment. Examples of such devices are disclosed in U.S. Pat. No. 4,320,759, U.S. Pat. No. 4,350,271 and U.S. Pat. No. 4,223,061.

DETAILED DESCRIPTION OF THE INVENTION

It has now been discovered that a three-phase system may be used to transfer active agents across the epidermis or across mucosal membranes by availing advantageously of Bernoulli fluid flow effects. Such systems deliver these active agents, together with a delivery fluid to a receiving surface. The delivery fluid serves to transport the active agent from the interior of the system to the interface between the device and the adjacent body surface. In biological systems transfer of substances across the epidermal layers or mucous membranes to capillary blood vessels takes place at a rate that is often controlled by the rate at which the substance is supplied to the biological surface. The system of the present device relies upon physico-chemical energy internal to the system to assure that there is always enough active agent available to be taken up by the biological surface. More particularly, Bernoulli fluid flow effects are advantageously employed to assure that an adequate amount of the agent arrives at the biological surface, and further that the additional pressure provided by the Bernoulli effect actually serves to increase the maximum possible diffusion rate of the agent through the skin or mucous membrane.

This novel three phase system is comprised of an outer portion, an inner portion and an active agent. Preferably, the outer portion is a polymeric foam having a pore size of approximately 1,000 pores per linear inch and it is so formed that it encompasses a void, wholly open at two ends. While various shapes may be used, a frustum shape having a longitudinal void is especially preferred. The inner portion is likewise preferably made from a polymeric foam but has a pore size of approximately 600 pores per linear inch and is so shaped as to fit snugly into the void formed by the outer portion. When the inner portion is in place, it should have a free surface at each of the free open ends of the outer portion. The third phase is the active agent comprising the medicament and is preferably in the form of a medicated gel, applied to the inner portion at some time prior to the joining of the inner and outer portions.

It is contemplated that the transdermal device may be packaged as its individual constituents as well as an integrated system. It is thus possible for the user to prepare a fresh application from medicament that has not been exposed to the atmosphere until immediately before use. This approach may often be necessitated by the use of active agents such as those that show some degradation upon lengthy exposure to the atmosphere. Also, by supplying the system as its individual components the user is afforded the opportunity to supply special medicaments or compositions and to vary concentrations of medicament, etc. in order to insure the optimal performance conditions for the desired therapy.

The active agent is applied through a free end of the inner portion. It is delivered to the point of application by the flow of delivery fluid from the outer surface of the microporous outer portion to the inner portion and then out of the free surface or surfaces of the inner portion. Such flow induction is set up by the Bernoulli effect which automatically drives the delivery fluid from regions of small pore size to regions of larger pore size. Preferably the shape and orientation of the device aid in further directing the fluid flow toward at least one of the free surfaces of the inner portion. Thus a fluid pressure somewhat greater than the ambient pressure is applied against the transfer surface. Such additional pressure serves to stabilize and enhance the rate of diffusion.

The inner and outer portions employed in the construction of the novel transdermal applicator are made from polymeric cellular foams such as those formed from polyester resin when water is used as a blowing agent. They may be made from many other polymeric resins, with the only requirements being their ability to form nonerodible cellular structures, and their being free of 1,4 dioxane, with a maximum content of 1 PPM TDA. Further examples of such materials include polyurethane, polyester, polypropylene or polyethylene resins. Such structures are desirably flexible for general use, so as to avoid undue irritation but may also be semi-rigid for specific applications such as, e.g., where the device is to be placed in a body region where there is likely to be great deforming stresses bearing on the device which would tend to compress it and thus impede its intended constant rate mode of operation. It is also important that the foam material be chosen to allow ease of die cutting or peeling into the desired shape.

It will usually be necessary for the two sections of the device to be manufactured in separate batches so that the resulting foams will have different pore sizes. The pore sizes of polymer matrices is a function of various processing parameters that can be appropriately controlled by one skilled in the art.

In order for the transdermal applicator to operate in accordance with the Bernoulli principle the foam portions must not have a homogenous pore structure, but instead must have a structure which provides local regions of relatively larger and smaller pore sizes. Such structures provide the framework that is necessary to set up a Bernoulli flow in which the delivery fluid is pulled from the outer to the inner portions of the device. Often the change in pore size between the outer and inner portions of the device occurs abruptly at the interface of the two portions.

But, this is not necessarily the case since devices within the scope of this invention may employ a graded system in which the pore sizes get progressively larger toward the inner region. Foams which give adequate results have pore sizes which range from 1,000 pores per linear inch to 3,500 pores per linear inch for the outer portion, and from 200 pores per linear inch to 600 pores per linear inch for the inner portion. The preferred ratio of large pore size to small pore size is 1.67 to 1 but this ratio may be increased to 2 to 1.

Availing of the Bernoulli effect is the key to the present invention and provides the force necessary to draw fluid from the saturated microporous outer portion through the medicament-impregnated gel and into the inner macroporous vortex chamber; the larger pores draw fluid from the smaller pores. According to the principle formulated by mathematician Daniel Bernoulli, the total energy at every point along a fluid flow surface remains constant so that as pressure decreases the velocity of the fluid within the system must increase. A third variable in such fluid flow systems is the cross-sectional area of the conduit or other orifice through which the fluid must flow. As the cross-sectional area of a system increases, the pressure decreases but when this occurs, as mentioned above, the velocity increases. Thus in the present system when the delivery fluid is migrating through the system, it first comes upon the region of smaller pore size and a local pressure effect results. The resulting pressure differential induces a flow of the delivery fluid from the outer portion of the device to the larger pore inner portion. Preferably the overall configuration of the device also serves to aid in concentrating the dissolved or dispersed medicament at the skin or mucosal membrane surface. Much as the Bernoulli effect pushes or draws water through a thin pipe into a wider pipe, the most preferred frustum shape of the device serves to direct the flow of the medicament-laden fluid entering the inner larger pore size vortex portion against the skin. The effect of the aforementioned directed flow is not only to concentrate the medicament at the skin surface, but to apply the medicament-laden fluid against the skin at a pressure higher than that of the surrounding atmosphere. Thus the rate of transdermal diffusion which would normally result from the concentration gradient of the dissolved medicament across the skin is here enhanced and increased by the pressure gradient which results from the novel construction of this device. Thus it can be seen that the system relies only upon its internal physico-chemical driving forces without the need for any externally applied forces.

At this point it should be noted that the effective operation of the system necessitates that there be substantial communication between the outer and inner portions so that a continuous path for the induced fluid flow is provided. The preferred method of assuring such intimate contact is through the use of an inner portion which is approximately ten percent larger than the void space cut in the outer portion. Such arrangements have the advantage of being readily separable and hence reusable. The present system is not, however, limited to this method and may take the form of a laminate or any other configuration which provides the communication of elements necessary to allow substantially unhindered flow of the delivery fluid. Further, it is contemplated that unitary devices having any requisite pore size distribution for inducing fluid flow will come within the scope of the present invention.

The device may take the shape of a frustum, a cylinder, a disc or any other form which may serve as a conduit for the flow of the delivery fluid into the inner portion wherein it picks up medicament and sweeps it out through at least one of the free surfaces of the inner portion. The truncated cone shape is greatly preferred for most transdermal applications. This shape serves to help direct the flow of the active agent laden fluid entering the inner portion or vortex chamber against the skin in much the same manner as the Bernoulli effect pushes or draws water through a thin pipe into a wider pipe. It is, of course, necessary to apply the device with the wide base against the skin. It is also necessary to have the narrow end of the vortex chamber, at the top of the frustum or disc, exposed to atmospheric pressures, e.g., it cannot be covered by an impermeable adhesive tape and preferably should be left uncovered and exposed to the air. The truncated cone shape also prevents uneconomical and inconvenient loss of medicament through the top of the inner portion, or the outer surface of the microporous outer portion as the active agent is directed irreversibly into the interior of the device and against the skin surface independently of any external forces. Despite these advantages of frustum shape or disc, this invention is not limited thereto and may advantageously employ outer and inner portions of a great variety of shapes, especially when the device is to be used for other than transdermal applications, e.g., a cylindrical or tubular shape is preferred when the device is used in a body cavity.

The outer surface of the macroporous inner portion may be loaded with a gel dispersed medicament by any convenient method, such as spraying or immersion. Such gel dispersed medicament is preferably a glycerogelatin comprised of glycerin, water, gelatin, and one or more medicinal or chemical substances which may conveniently be used as a rolled strip to coat the macroporous inner portion. The medicament may, of course, be composed of other substances but it is generally preferred that the gel be a soft solid that melts at body temperature and can safely be applied to the skin or mucous membrane, e.g., it is not an irritant. Gelatin acts as an emollient or buffer in the medicated gel which, while providing stability to the medicaments, limits trauma to the epidermis and mucousal membranes of the body.

The composite device may be attached to the skin, with the wide base of the truncated cone held against the skin surface by any suitable attachment means including adhesive tape, but care must be taken not to obstruct the narrow region of the vortex chamber distal to the skin surface.

To use the device, the microporous outer portion of the device is charged with a fluid. Preferably this is water but it may be any of various known wetting agents or medicament-miscible fluids that are not irritating to skin or mucose. For example, where deep penetration is required, such as to deliver an anesthetic through the lower lip, a combination of water and a penetrant such a liquid glycerin may be advantageously employed. To charge the device and commence its operation, water or other delivery fluid is added to and allowed to soak into the microporous outer portion. The volume of delivery fluid will depend upon the size of the device and should saturate the microporous outer portion for optimal performance. The length of time of release and the magnitude of the doses are dependent upon the thickness and density of the applied medicament, and the outer portion can be rewetted as necessary over the course of prolonged treatment, e.g., 48 hours, as necessary. Bottled water or tap water can be used, since any impurities will be filtered and retained in the pores of the outer portion.

Many active agents can be advantageously used with the present invention. Often the particular medicament used defines the physical characteristics of the system. This follows from the fact that the medicament is most benefically applied directly to the afflicted area. For example, pilocarpine, a drug used to treat glaucoma, may advantageously be applied directly to the eye of the patient when it is transferred through an embodiment of the present invention which is placed below the lower eyelid. Other medicaments that may be used with specifically tailored embodiments of the application include chemotherapeutic and contraceptive agents. Typical chemotherapeutic agents that may be used are adriamycin and cisplaten. The use of these drugs with the present device may take advantage of the circadian rhythms (the changes that occur regularly during a 24 hour period in such bodily characteristics as temperature, blood cell count and cell division rate) to mitigate the toxic effects these drugs have on biological systems. Since most chemotherapeutic agents attack rapidly dividing cells, such as stomach cells, the maximum safe dosage varies throughout the day depending upon the division rate of normal body cells. Thus in order to obtain the maximum benefit available from chemotherapeutic agents it is necessary to tightly control the amount of such agents being absorbed by the body. Such control may be obtained by two general approaches. First, the applicator may be placed near the site of the tumor so as to supply the most concentrated medicament directly without first circulating throughout the body or passing through the gastrointestinal tract. Second, the diffusion rate of the agent through the skin or mucosa may be controlled by adjusting the chemical energy exerted by the system. This may be accomplished by changing the size of the applicator, adjusting the amount of delivery fluid placed on the microporous outer portion, and adjusting the amount of medicament loaded into the inner portion.

Livestock are routinely administered antibiotic and other drugs by either dietary supplementation or parenteral booster injections. Both such treatment means require the administration of significant amounts of medicine, even for routine prophylaxis. A transdermal applicator of the present invention attached, e.g., to the inner ear of a cow, can administer an effective and continuous dose which is titered at low concentration over a period of several days.

In this way excessive systemic concentrations of the administered drug are avoided, and the likelihood that the drug will be stored or sequestered in the meat or consumable tissues, or e.g., in the milk of cows, is substantially lessened. This in turn reduces the danger that humans who consume milk or meat will be unnecessarily exposed to the antibiotic or other drug, and reduces the likelihood of developing unwanted immunity, via mutation or plasmid transfer, to the action of the drug.

Iodine is a substance that is required for carrying out many normal bodily functions such as thyroid regulation. Commonly iodine tablets are supplied in a biologically usable form for the treatment of hyperactive thyroid conditions and as an antiradiation medication. Various receptors are located throughout the body which require iodine in order to allow the biosystem which they are associated with to function properly. When there is an iodine deficiency not only do bodily systems function inefficiently, but there is a greater risk that radioactive iodine will accumulate and damage surrounding tissue. As mentioned, iodine tablets have been used to remedy these problems, but the tablets have the disadvantage of being difficult to digest and result in the characteristic concentration swings associated with oral medications. The transdermal applicator, when worn over the thyroid or behind the left knee, can be used to supply the iodine necessary to prevent a deficiency and at the same time avoid the digestion problems associated with tablets. It has been found that this invention can be used with potassium iodide to block ninety percent of the radioactive iodine immediately after exposure and still block fifty percent three to four hours after exposure, and may be safely positioned for fetal blocking. Alternatively, a solution of elemental iodine, potassium iodide, alcohol, and ammonia, commonly referred to as white iodine, may be employed.

Many medicaments that are available for vaginal dispersion are particulary beneficial when used with the novel transmucosal system. Contraceptives and agents which attack vaginal infections and venereal diseases such as kanamycin sulfate, nystatin and nonoxynol-9 are particularly beneficial when used with the present system. In such embodiments, aqueous body fluids are absorbed into the outer portion and activate the system to deliver medicament without external activation.

In one embodiment of the invention a polymer matrix containing weakly linked nonoxynol-9 serves as the macroporous inner portion of the device. The cellular foam of this embodiment releases spermicidally active nonoxynol-9 into a body cavity at a constant rate until mechanical pressure such as that generated during coitus is applied, whereupon the nonoxynol is released at high concentration. Preferably such polymer matrices will contain approximately 5% to 9% nonoxynol-9. The chemical properties of octoxynol or nonoxynol-9 allow it to weakly link with anionic polymer substrate under acidic conditions.

The following example describes one method for producing polymer matrices having the above-described properties.

EXAMPLE

| | |
|---|---|
| Polyester Resin (Witco Chemical Foam Resin) | 100 parts by wt. |
| Octoxynol or nonoxynol-9 (Polytergent B300-Olin Corporation) | 2 parts by wt. |
| Toluene Diisocyanate (BAFS Wyandotte) | 2 parts by wt. |
| Tertiary Amines | .01 % by wt. |
| Aliphatic Isocyanate | .01 % by wt. |
| Silicone Surfactants (Organo-Union Carbide) | .01 % by wt. |

The inner portion of the device is formed metering all of these components into a mixing head. While these components are being continuously mixed under a blanket of dry air, water is added as a blowing agent. The resulting product is then cured at 51° for three days after vacuuming to remove ethylene gas residuals. Alternatively, the following cure cycle may be used to produce a more linear polymer:

(a) −35° C. for one night;
(b) −45° C. during the following day;
(c) 60° C. during the next night.

The low initial curing temperature yields a more linear polymer which is more easily sectioned than the highly crosslinked polymers. Blocks may be cut on the morning following completion of the polymerization, but aging improves the ease of cutting.

The outer portion may be formed in the same manner as the inner portion with the exception that no octoxynol or nonoxynol-9 is added to the mixture, and, of course the processing conditions are varied so that the pore size of the outer portion will be smaller than that of the inner portion.

DESCRIPTION OF DRAWING

In FIG. 1, macroporous inner portion 2 is disposed within microporous outer portion 1 and has upper and lower free surfaces 3 and 4 located on each base of the disc or the frustum shaped embodiment.

Figure 1:
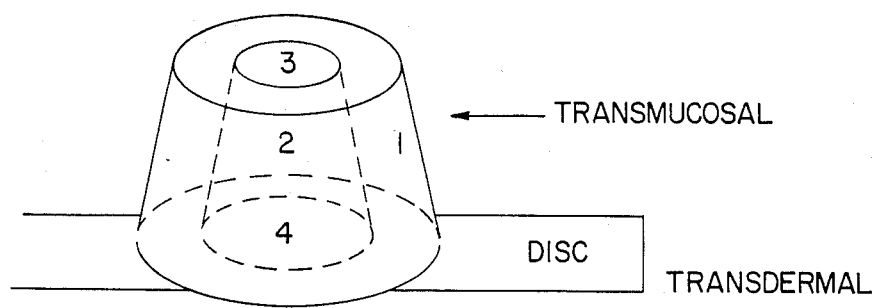
FIG. 1 shows the preferred embodiment of the present invention.

I claim:

1. A device for delivery of medicaments to epidermal and mucosal surfaces comprising:
   (a) a microporous outer portion made from polymeric foam, and
   (b) A macroporous inner portion made from polymeric foam disposed within the outer portion and in substantial communication therewith which is adapted for the incorporation therein of a medicament,
   wherein the macroporous inner portion has at least one free surface not in communication with the microporous outer portion, the pore size ratio of the macroporous inner portion to the microporous outer portion is between about 2 to 1 and 1.67 to 1.

2. A device as recited in claim 1, wherein the device is disc shaped.

3. A device as recited in claim 1, wherein said device is frusto-conical in shape.

4. A device as recited in claim 1, wherein said device is cylindrical in shape.

5. A device as recited in claim 1, wherein the polymeric foam is a polyester, polyethylene or polypropylene.

6. A device as recited in claim 1, wherein said microporous outer portion has 1,000 pores per linear inch and said macroporous inner portion has 200 pores per linear inch.

7. A device as recited in claim 1, further comprising an adhesive strip attached to the outer surface of said device.

8. A device for delivery of medicaments to epidermal and mucosal surfaces comprising:
   (a) a microporous outer portion made from polymeric foam;
   (b) a macroporous inner portion made from polymeric foam disposed within the outer portion and in substantial communication therewith which is adapted for the incorporation therein of a medicament; and
   (c) a medicament incorporated in the macroporous inner portion,
   wherein the macroporous inner portion has at least one free surface not in communication with the microporous outer portion, and the pore size ratio of the macroporous inner portion to the microporous outer portion is between about 18:1 and 1.67:1.

9. A device as recited in claim 8 wherein said device is disc shaped.

10. A device as recited in claim 8, wherein said device is frusto-conical in shape.

11. A device as recited in claim 8, wherein said device is cylindrical in shape.

12. A device as recited in claim 8, wherein the polymeric foam is a polyester foam free of 1,4 dioxane, with a maximum content of 1 PPM TDA.

13. A device as recited in claim 8, wherein the medicament is supplied as a medicated gel.

14. A device as recited in claim 13, wherein the medicated gel comprises glycerin, water, gelatin and one or more water soluable medicaments.

15. A device as recited in claim 13, wherein the medicated gel is coated on the exterior of the macroporous inner portion.

16. A device as recited in claim 8, wherein the medicament is a chemotherapeutic agent.

17. A device as recited in claim 8, wherein the medicament is a spermicidal agent.

18. A device as recited in claim 17 wherein the spermicidal agent is nonoxynol-9 or octoxynol, and it is incorporated within the polyester foam matrix forming the macroporous inner portion.

19. A device as recited in claim 8, wherein the medicament is an antibacterial agent.

20. A device as recited in claim 8, wherein the medicament is a thyroid regulator.

21. A device as recited in claim 8, wherein the medicament is potassium iodide (KI) an antiradiation medicament for use as a radioiodine blocker.

22. A device as recited in claim 8, wherein the medicament is a hormone.

23. A device as recited in claim 8, wherein the medicament is insulin.

* * * * *